US005156802A

United States Patent [19]

Robertson et al.

[11] Patent Number: 5,156,802

[45] Date of Patent: Oct. 20, 1992

[54] INSPECTION OF FUEL PARTICLES WITH ACOUSTICS

[75] Inventors: Michael O. Robertson, Hurt; Donald M. Stevens, Lovingston; Hubert L. Whaley, Lynchburg, all of Va.

[73] Assignee: The Babcock & Wilcox Company, New Orleans, La.

[21] Appl. No.: 761,204

[22] Filed: Sep. 17, 1991

Related U.S. Application Data

[62] Division of Ser. No. 669,826, Mar. 15, 1991.

[51] Int. Cl.[5] .............................................. G21C 17/00

[52] U.S. Cl. .................................... 376/245; 376/261; 73/12; 73/579; 73/150 R; 209/599; 209/656; 209/908

[58] Field of Search ........................ 376/245, 252, 261; 73/12, 579, 150 R; 209/590, 656, 599, 908

[56] References Cited

U.S. PATENT DOCUMENTS

| | | | |
|---|---|---|---|
| 2,393,225 | 1/1946 | Andalikiewicz | 73/69 |
| 3,127,016 | 3/1964 | Baigent | 209/74 |
| 4,147,620 | 4/1979 | Artiano et al. | 209/590 |
| 4,149,075 | 4/1979 | Druckier et al. | 250/336 |
| 4,212,398 | 7/1980 | Parker et al. | 209/590 |
| 4,227,081 | 10/1980 | Caputo et al. | 250/321 |
| 4,466,543 | 8/1984 | Zwahlen et al. | 209/556 |
| 4,608,869 | 9/1986 | Lerner | 73/644 |
| 4,620,445 | 11/1986 | McKendree et al. | 73/647 |
| 4,620,716 | 7/1986 | Barla-Szabó et al. | 209/599 |
| 4,633,714 | 1/1987 | Mazumder et al. | 73/596 |
| 4,665,760 | 5/1987 | Eramo et al. | 73/866.5 |
| 4,890,920 | 1/1990 | Nizioleh et al. | 356/336 |
| 4,894,201 | 1/1990 | Ahmed | 376/261 |
| 4,944,185 | 7/1990 | Clark, Jr. et al. | 73/579 |
| 5,046,362 | 9/1991 | Strubbe | 73/579 |

FOREIGN PATENT DOCUMENTS

| | | | |
|---|---|---|---|
| 2506212 | 8/1975 | Fed. Rep. of Germany | 209/599 |
| 2635993 | 3/1990 | France | 209/599 |

OTHER PUBLICATIONS

Battle, D. J., Scruby, C. B., "Characterization of Particle Impact by Quantitative Acoustic Emission", *Wear*, vol. 137, pp. 63-90, 1990.

*Primary Examiner*—Donald P. Walsh
*Assistant Examiner*—Chrisman D. Carroll
*Attorney, Agent, or Firm*—Vytas R. Matas; Robert J. Edwards; Daniel S. Kalka

[57] ABSTRACT

An apparatus and method are disclosed for determining the integrity of coated fuel particles via acoustic characterization. Particle supply means (4) drops the nuclear fuel particles (2) individually onto the face (6) of a transducer (8). The generated signal which is indicative of the integrity of the coating on the dropped particle is analyzed with analyzing means (26, 28, 30) for discriminating between a flawed and an unflawed particle.

5 Claims, 2 Drawing Sheets

INSPECTION OF FUEL PARTICLES WITH ACOUSTICS

This invention was made with Government support under Contract No. SDI084-89-C-0001 awarded by the U.S. Department of Defense (DOD). The Government has certain rights in this invention.

This is a division of application Ser. No. 07/669,826 filed Mar. 15, 1991.

BACKGROUND OF THE INVENTION

1. Field of the Invention

The present invention relates in general to an acoustic characterization technique for particle integrity, and in particular, to an acoustic characterization technique for determining the integrity of outer coatings on nuclear fuel particles.

2. Description of the Related Art

In a new design particle bed reactor (PBR), a typical fuel rod consists of millions of tiny multi-layered spherical fuel particles, each having a nominal diameter of roughly about 500 microns (μm). The innermost "kernel" of each particle consists of enriched uranium. The intermediate layers of each particle consist of buffering carbon layers. The outermost layer of each particle consists of a thin coating of a metallic carbide whose primary purpose is to serve as a barrier against escaping fission products. It is readily understood that maintaining the integrity of the fuel particle's outer carbide layer is of the utmost importance.

Currently, there are only a few inspection techniques applicable to determining the integrity of such particles. Most of these techniques are destructive in nature, and all of the prior art techniques are applicable to only a small percentage of a given batch or lot of particles.

Accordingly, there is a need for an inspection technique for determining the integrity of a nuclear fuel particle which is nondestructive in nature and can inspect each particle quickly and reliably.

SUMMARY OF THE INVENTION

The present invention solves the aforementioned problems with the prior art as well as others by providing an apparatus and method for acoustic characterization of the integrity of the coating on nuclear fuel particles. In the present invention, the particles to be tested are individually dropped on a piezoelectric acoustic transducer to generate an electrical signal indicative of the integrity of the coating on the dropped particle. Signal analysis is then utilized to discriminate between a flawed and unflawed particle by comparing each signal response with that of a calibrated standard of an unflawed particle.

In the preferred embodiment, the signal analysis means comprises an amplifier and an analog-to-digital (A/D) converter to amplify the signal and input it into a computer which houses digital analysis software. Differences in the signal response enable discrimination between flawed and unflawed particles.

Accordingly, an object of the present invention is to provide an acoustic technique for fuel particle inspection which enables 100% inspection of the particles in a reasonable time frame.

Another object of the present invention is to provide a nondestructive acoustic characterization apparatus and method for determining the integrity of the coating on nuclear fuel particles.

Still another object of the present invention is to provide a simple, inexpensive apparatus and method for acoustically discriminating between flawed and unflawed particles.

The various features of novelty which characterize the invention are pointed out with particularity in the claims annexed to and forming part of this disclosure. For a better understanding of the present invention, and the operating advantages attained by its use, reference is made to the accompanying drawing and descriptive matter in which the preferred embodiment of the invention is illustrated.

DESCRIPTION OF THE PREFERRED EMBODIMENT

The present invention resides in an apparatus and method for determining the integrity of the coating of nuclear fuel particles via acoustic characterization. 100% inspection capability is achieved with the present invention for millions of coated nuclear fuel particles associated with particle bed reactors as is well known in that art.

Figure 1:
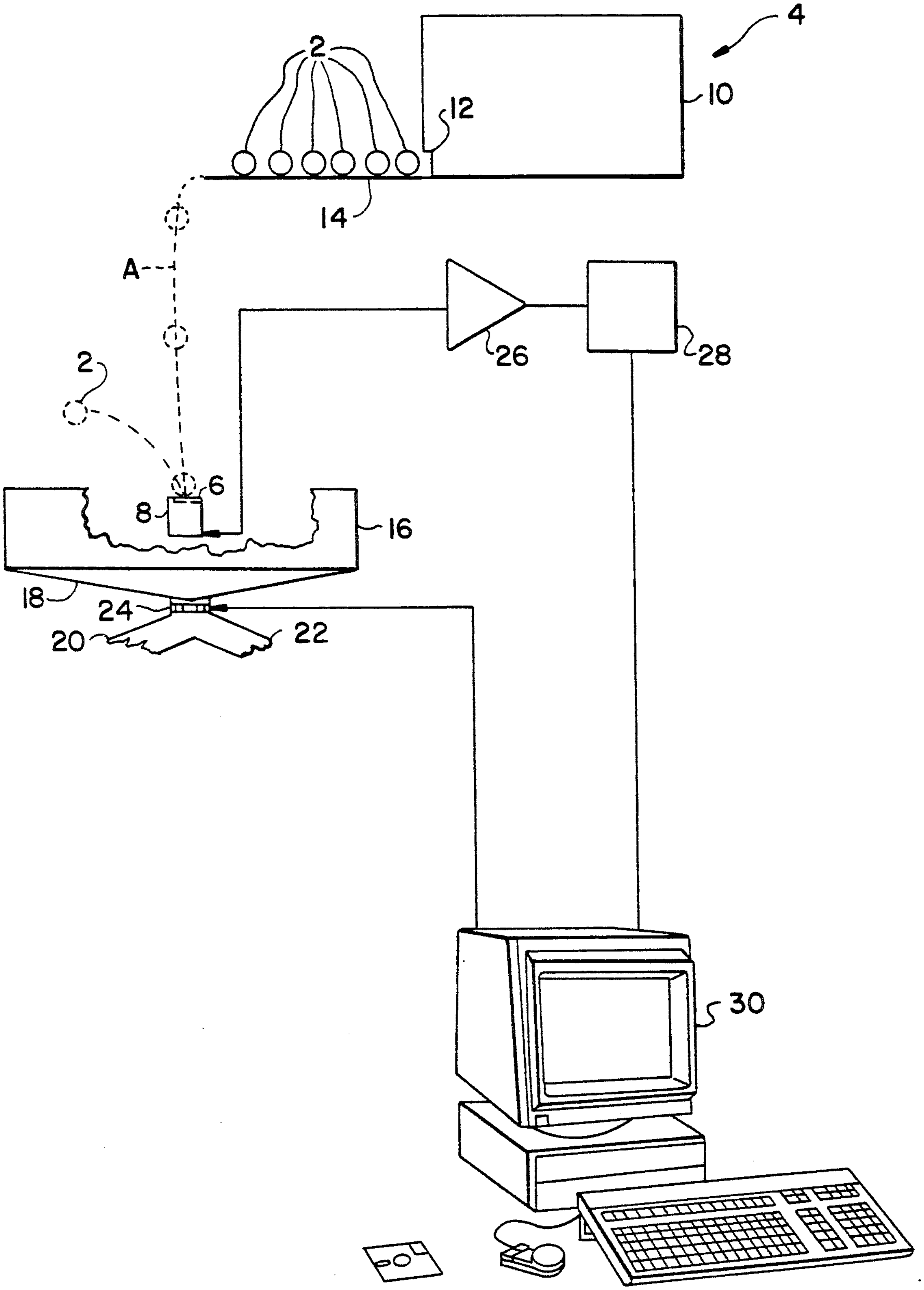
FIG. 1 is a schematic view of the fuel particle acoustic inspection system in accordance with the present invention.

Referring to FIG. 1, there is illustrated a schematic representation of the present invention. Fuel particles (2) from a particle supply means (4) are individually dropped, as depicted by the dashed line A (with the dropped particle also being depicted in dashed line form), onto the face (6) of a transducer (8) such as a piezoelectric acoustic transducer.

The particle supply means (4) is any suitable device for dropping particles individually on transducer (8). For illustrative purposes one example may include a hopper (10) with an opening (12) which allows a single particle to roll down a chute (14) where it drops on the transducer (8). Of course, other suitable particle supply means (4) only need to drop particles from a supply individually on the transducer (8).

At the time of impact, a compressional impulse is generated at the point of contact of the particle (2) and the transducer face (6). A compressional impulse wave propagates diametrically through the fuel particle which is spherical and is reflected at the opposite surface as a tensile impulse wave. The tensile impulse wave then makes a return journey through the spherical nuclear fuel particle with the particle snapping away from the transducer when the impulse reaches the starting point of contact between the particle (2) and the transducer face (6). Of course, it is realized that this entire process takes only a fraction of a microsecond. The dropped particle (2) is then collected in another basket or hopper (16) with means for separating flawed from unflawed particles.

Suitable separating means need only remove a batch or small portion of particles containing a flawed particle. Ideally, the separating means would remove only the flawed particle, but even removing some unflawed particles with the flawed one is acceptable. FIG. 1 illustrates one example including a hopper (16) with a slanted portion (18) to collect the dropped particles. Channels (20, 22) connected to hopper (16) allow for separation of the flawed particles through channel (22) while the unflawed particles pass through channel (20). Gate (24) selectively controls the opening of the channels (20, 22) where they are disposed of or collected in a known manner. Gate (24) may be connected to the control system or a computer (30) for automatic operation. Any suitable separating means may be employed with the present invention and this example is not intended to limit the invention hereto.

During the period of intimate contact between the fuel particle (2) and the transducer face (6), part of the vibrational resonance of the particle is redistributed as elastic waves in the transducer face (6) and convolved with the transducer (8) response itself. The resulting signal is thus a combination of transducer (8) response and the signal derived from the particle (2). The signal from transducer (8) is amplified with amplifier (26) and sent to an analog-to-digital (A/D) converter (28) prior to being input into a computer (30) housing digital analysis software. Differences in the signal response as depicted in FIG. 2 as viewed from the computer enable discrimination between flawed and unflawed particles.

Figure 2:
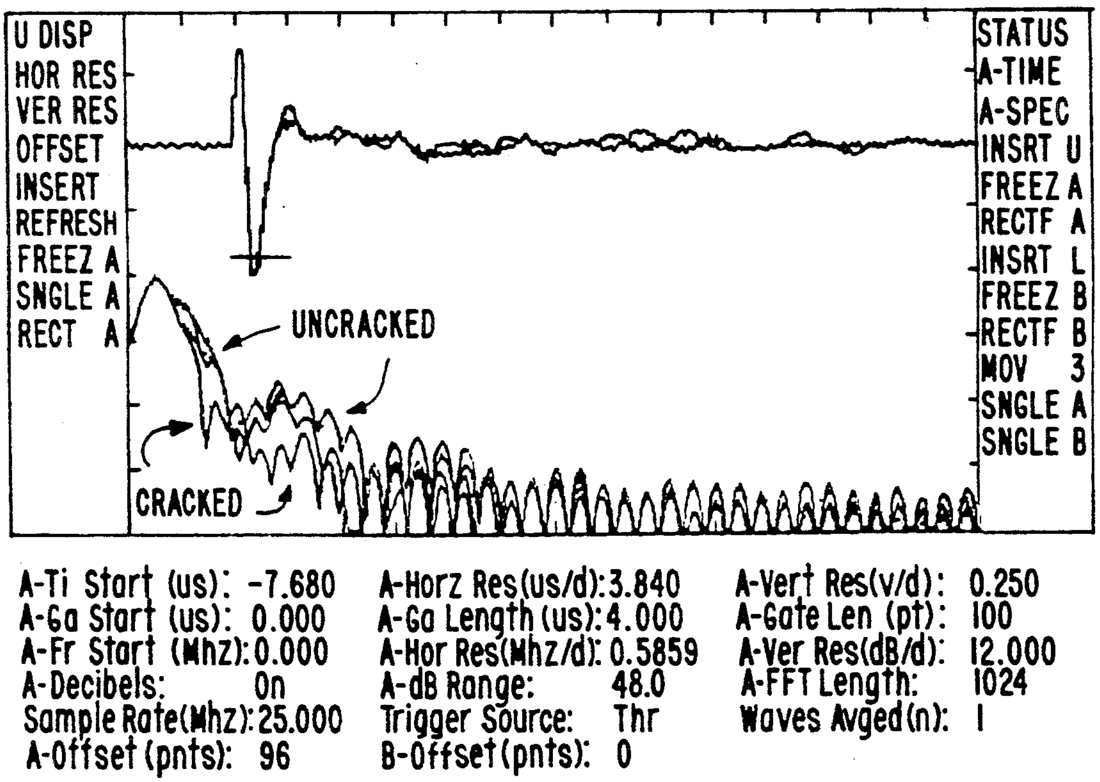
FIG. 2 is an illustration of an unflawed and flawed particle response.

The "good" particle response as shown in FIG. 2 as "uncracked" preferably is a calibrated standard signal which is the basis for the comparison. In an alternate embodiment, this calibration may be performed with stored data points so that a visual inspection is not necessary. The sample to be tested generates a curve with data points that are compared to the preset values.

Cracked or flawed particles when struck by an impulse tend to resonate at a different frequency from their homogeneous counterparts as seen in FIG. 2. Hence, a cracked fuel particle (i.e., outer layer of zirconium carbide (ZrC) cracked), when dropped onto the face (6) of a piezoelectric transducer (8), generates a significantly different signal from that of a non-cracked particle. By analyzing signal responses, the acoustic discrimination technique of the present invention is able to discriminate flawed from unflawed fuel particles.

Any variation of particle integrity, e.g., laminations, cracks, nonsphericity can give rise to subtley different signal signatures. Consequently, the system is trained to globally inspect the particle and look for any variations in the signal to allow for a general inspection technique. Once calibrated for a known acceptable particle, the system is used to screen out any particle that gives a signal response that fails to fit the "good" pattern.

While a specific embodiment of the present invention has been shown and described in detail to illustrate the application and principles of the invention, it will be understood that it is not intended that the present invention be limited hereto and that the invention may be embodied otherwise without departing from such principles.

What is claimed is:

1. A method for acoustically inspecting the coating integrity of the outer carbide layer of a nuclear fuel particle, comprising the steps of:

providing a supply of nuclear fuel particles for inspection;

dropping a nuclear fuel particle to be inspected from the supply one at a time on an acoustic transducer;

generating from each nuclear fuel particle impact on the acoustic transducer a signal indicative of the integrity of the outer carbide layer for each of the dropped nuclear fuel particles;

analyzing each signal digitally for discriminating from a flawed and an unflawed nuclear fuel particle based on calibrated signals; and separating a flawed nuclear fuel particle from an unflawed nuclear fuel particle.

2. A method as recited in claim 1, further comprising the step of collecting unflawed nuclear fuel particles in a hopper.

3. A method as recited in claim 2, further comprising the step of collecting the flawed nuclear fuel particles in a second hopper.

4. A method as recited in claim 1, wherein each of said nuclear fuel particles has a diameter of about 500 microns.

5. A method as recited in claim 1, wherein each of said nuclear fuel particles has an innermost kernel of enriched uranium surrounded by intermediate layers of buffering carbon with an outermost layer of the metallic carbide which serves as a barrier against escaping fission products.

* * * * *